United States Patent
Ergler et al.

(10) Patent No.: US 9,636,078 B2
(45) Date of Patent: May 2, 2017

(54) IMAGING MEDICAL DEVICE

(71) Applicant: Siemens Aktiengesellschaft, Munich (DE)

(72) Inventors: Thorsten Ergler, Forchheim (DE); Steffen Kappler, Effeltrich (DE); Björn Kreisler, Hausen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 313 days.

(21) Appl. No.: 14/566,853

(22) Filed: Dec. 11, 2014

(65) Prior Publication Data
US 2015/0182183 A1 Jul. 2, 2015

(30) Foreign Application Priority Data

Dec. 30, 2013 (DE) .......................... 10 2013 227 214

(51) Int. Cl.
*A61B 6/00* (2006.01)
*A61B 6/03* (2006.01)

(52) U.S. Cl.
CPC ................ *A61B 6/56* (2013.01); *A61B 6/035* (2013.01); *A61B 6/4488* (2013.01)

(58) Field of Classification Search
CPC ....... A61B 6/032; A61B 6/4488; A61B 6/035; A61B 6/56; A61B 2017/00084; G01N 23/046
See application file for complete search history.

(56) References Cited

U.S. PATENT DOCUMENTS

| 2005/0206769 A1 | 9/2005 | Kump et al. |
| 2005/0207534 A1 | 9/2005 | Petrick et al. |
| 2011/0110498 A1 | 5/2011 | Takae et al. |

(Continued)

FOREIGN PATENT DOCUMENTS

| CN | 102085768 A | 5/2011 |
| DE | 102005014119 A1 | 10/2005 |

(Continued)

OTHER PUBLICATIONS

Chinese Office Action and English translation thereof dated Dec. 28, 2016.

*Primary Examiner* — Hoon Song
(74) *Attorney, Agent, or Firm* — Harness, Dickey & Pierce, P.L.C.

(57) ABSTRACT

An imaging medical device includes a detector including an active material which is serviceable in a state of thermodynamic equilibrium, a primary power supply designed to supply the imaging medical device with power in an operating state, and an ancillary power supply designed to maintain a thermodynamic equilibrium in the active material of the detector in a non-operating state of the imaging medical device to keep the detector in a state of readiness. A method for operating such an imaging medical device is disclosed, wherein in the operating state, the imaging medical device is supplied with power via the primary power supply, and wherein in the non-operating state, a thermodynamic equilibrium is maintained in the active material of the detector, with power supplied by the ancillary power supply. The detector is thereby kept in a state of readiness.

18 Claims, 1 Drawing Sheet

(56) References Cited

U.S. PATENT DOCUMENTS

| | | | | |
|---|---|---|---|---|
| 2011/0311023 A1* | 12/2011 | Sagoh | ............ | A61B 6/032 378/19 |
| 2012/0020453 A1* | 1/2012 | Kanemaru | ............ | A61B 6/4488 378/15 |
| 2012/0033784 A1* | 2/2012 | Matsuda | ............ | A61B 6/00 378/19 |
| 2013/0279648 A1* | 10/2013 | Joshi | ............ | A61B 6/03 378/19 |
| 2014/0153689 A1* | 6/2014 | Anno | ............ | H05G 1/025 378/4 |

FOREIGN PATENT DOCUMENTS

| | | |
|---|---|---|
| JP | 2003052136 A | 2/2003 |
| JP | 2010273782 A | 12/2010 |

\* cited by examiner

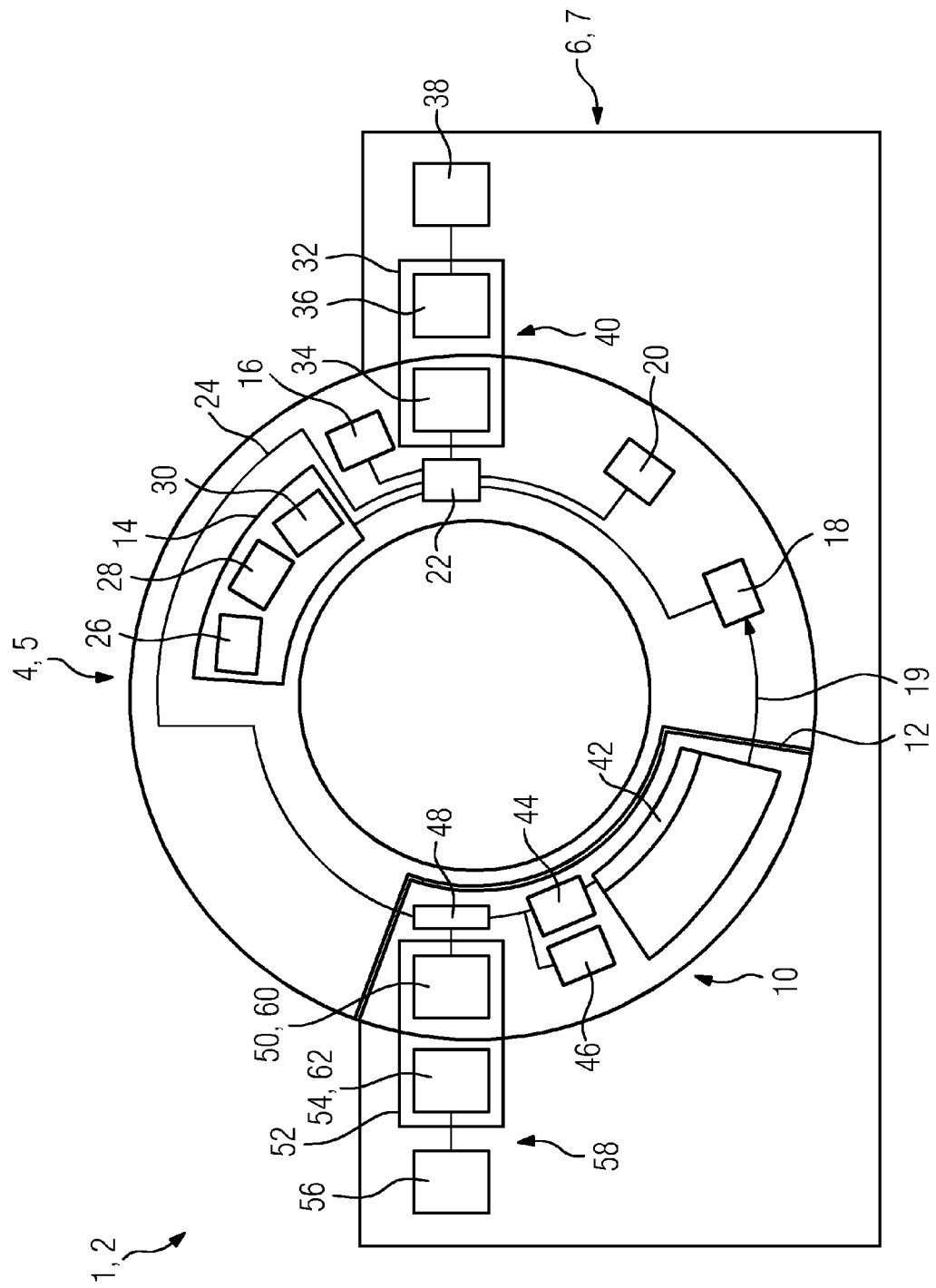

IMAGING MEDICAL DEVICE

PRIORITY STATEMENT

The present application hereby claims priority under 35 U.S.C. §119 to German patent application number DE 102013227214.6 filed Dec. 30, 2013, the entire contents of which are hereby incorporated herein by reference.

FIELD

At least one embodiment of the invention generally relates to an imaging medical device which comprises a detector having an active material which is serviceable in a state of thermodynamic equilibrium, and a primary power supply, wherein the primary power supply is designed to supply the imaging medical device with power in an operating state. The invention further relates to a method for operating such an imaging medical device.

BACKGROUND

In a modern computed tomography system, a direct conversion X-ray detector based on cadmium telluride or cadmium zinc telluride is in particular used for photon-counting applications. After being taken into operation such a detector exhibits a counting rate drift which can result in artifacts during the imaging process. In order to achieve a reliable, high-resolution and interference-free image generation it is necessary for the cadmium telluride or the cadmium zinc telluride to have reached a stable state of equilibrium in respect of an occupation of impurities following the operation of turning on the computed tomography system.

Such a state of equilibrium of the impurity occupation is dependent in this situation on the voltage present at the X-ray detector. The attainment of a state of equilibrium adequate for artifact-free image generation after switching on a high voltage at the X-ray detector is a process which can extend over a period of several hours. With regard to use in day-to-day medical practice it is desirable for reasons of efficiency for the computed tomography system to be available ready for operation on as permanent a basis as possible. On the other hand, the extended period of time required to reach the state of equilibrium would result in a considerable loss of time for examinations in the event of a daily power-up procedure in practical operation. One could therefore be inclined to consider running the power supply of the X-ray detector continuously.

An X-ray detector is arranged on the rotating assembly of the computed tomography system together with a plurality of other consumer loads, for example the X-ray tube, image-processing electronics components as well as coolers and fans. Said consumer loads, with the exception of the anode voltage of the X-ray tube, constitute a continuously operated basic load of several kW. On account of said basic load, uninterrupted operation of the rotating assembly, in other words including nights and weekends, in order to maintain the state of equilibrium in the X-ray detector would be inefficient in terms of energy use.

As a possible way of avoiding this, the primary power supply to the consumer loads on the rotating assembly could be configured in such a manner as to have two switching or operating states, where in primary operation all the consumer loads and in ancillary operation only the X-ray detector are/is supplied with power. Such a procedure would however require that the power distributor of the rotating assembly would need to be designed with intelligence for switching off individual consumer loads, and would in this case itself need to undertake to differentiate the two operating states in a control electronics unit specially designed for the purpose because all the other electronics components would be switched off in ancillary operation.

The control electronics unit would for its part need to be incorporated into the communication between the other electronics components, in which case it would be necessary to consider that on the transition from ancillary to primary operation the remaining components first undergo their system startup before they have a full communications capability, in other words signal errors could occur while the control electronics unit of the power supply is already in operation. Such a solution by way of a division of the primary power supply would thus be susceptible to faults, which not least against the background of the high requirements for particularly stable operation in the medical sector, which are also reflected in approval procedures, results in such a solution variant being discarded.

SUMMARY

At least one embodiment of the invention is directed to an imaging medical device which is capable of placing a detector having an active material which is serviceable in a state of thermodynamic equilibrium in a state ready for operation as quickly and simply as possible. A further embodiment of the invention is directed to a method for operating such an imaging medical device.

An imaging medical device of at least one embodiment, comprises a detector having an active material which is serviceable in a state of thermodynamic equilibrium, a primary power supply which is designed to supply the imaging medical device with power in an operating state, and an ancillary power supply which is designed to maintain a thermodynamic equilibrium in the active material of the detector in a non-operating state of the imaging medical device in order to keep the detector in a state of readiness.

A method is disclosed, in at least one embodiment, for operating such an imaging medical device, wherein in the operating state the imaging medical device is supplied with power by way of the primary power supply, and wherein in the non-operating state a thermodynamic equilibrium is maintained in the active material of the detector with power supplied by the ancillary power supply, and the detector is hereby held in a state of readiness.

In a further advantageous embodiment of the invention, the imaging medical device is designed as a computed tomography system, wherein the static device part comprises a retaining frame, wherein the movable device part comprises a rotating assembly, and wherein the computed tomography system has a control unit which is designed to transport the movable device part into an idle position when the primary power supply is switched off. A computed tomography system configured in such a manner in particular offers the advantage of being able to hold the detector permanently in operational readiness with a comparatively low power draw.

BRIEF DESCRIPTION OF THE DRAWINGS

An example embodiment of the invention will be described in detail in the following with reference to a drawing. In the drawing:

FIG. 1 shows a schematic diagram of a computed tomography system having an ancillary power supply for the detector arranged on the rotating assembly.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the FIGURES.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the FIGURE. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the FIGURES. For example, two FIGURES shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the FIGURES. It will be understood that the spatially relative terms are intended to encompass different orientations of the device in use or operation in addition to the orientation depicted in the FIGURES. For example, if the device in the FIGURES is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An imaging medical device of at least one embodiment, comprises a detector having an active material which is serviceable in a state of thermodynamic equilibrium, a primary power supply which is designed to supply the imaging medical device with power in an operating state, and an ancillary power supply which is designed to maintain a thermodynamic equilibrium in the active material of the detector in a non-operating state of the imaging medical device in order to keep the detector in a state of readiness.

The active material of the detector is, in at least one embodiment, the material which the radiation emitted by the device for the examination impinges on, which radiation is possibly scattered by a sample under examination, and said radiation is converted optically or electro-optically by a physical process, in particular into a light signal or a current signal or voltage signal. The serviceability of the active material in this case is to be understood as a state in which an image capture operation of at least adequate image quality and resolution can be performed by the imaging medical device. A state of thermodynamic equilibrium in this case comprises inter alia a defined distribution of impurities in the material. In particular, a state of thermodynamic equilibrium also encompasses a state which exhibits a merely electrodynamic equilibrium.

The non-operating state is understood as the state in which the primary power supply is switched off. In the operating state the primary power supply supplies in particular the detector and a significant number of further consumer loads on the imaging medical device with power. If the imaging medical device has a plurality of power supply circuits which are completely separate from one another, then the primary power supply is understood to be the power supply which supplies the detector and a number of further consumer loads with power during an image capture operation and in the timeframe of such an image capture operation.

A method is disclosed, in at least one embodiment, for operating such an imaging medical device, wherein in the operating state the imaging medical device is supplied with power by way of the primary power supply, and wherein in the non-operating state a thermodynamic equilibrium is maintained in the active material of the detector with power supplied by the ancillary power supply, and the detector is hereby held in a state of readiness.

At least one embodiment of the invention is based on the consideration that it can take up to several hours to attain a state of thermodynamic equilibrium, depending on the type thereof, and therefore the active material of the detector can most simply be placed into a state of operational readiness if the state of equilibrium is maintained permanently. This implies a permanent supply of power to at least the detector. Since a complex interplay of different electronics components which communicate with one another for the purpose of image generation and processing often takes place in an imaging medical device, a division of the primary power supply into supply elements which can be individually switched on and off is not desirable because this could in particular have a negative influence on the common time synchronization and thus the communication of image-processing electronics components. In particular in medical devices, however, particularly stable and reliable operation is frequently desired.

An ancillary power supply, which is principally designed to keep the detector in a serviceable state in the non-operating state of the primary power supply, would in the first instance likewise be rejected for reasons of both space and cost. A core realization of the invention is however the fact that the system complexity of the overall imaging medical device which is only slightly increased by an ancillary power supply to the detector can be compensated for by the advantage of the detector in principle being permanently in a state of potential operational readiness.

The detector is preferably designed as an X-ray detector. Particularly in an X-ray detector, a material which should be placed under voltage over an extended state and/or cooled or heated in order to attain a serviceable state is often employed as the active material.

To this end, at least one device for heating and/or for cooling, which have a connection to the ancillary power supply, can expediently be arranged on the detector. In particular in this situation an ohmic heater, a cooler or a fan can be included, which in each case can be supplied with power in the non-operating state by the ancillary power supply. In particular, a cooler and/or a fan and/or a heater can also be used in this case, which is supplied in the operating state by the primary power supply, and is also designed to keep the active material of the detector serviceable in the operating state.

It proves to be advantageous if the imaging medical device has a static device part and a movably mounted device part attached thereto, wherein the detector is arranged on the movable device part, wherein the primary power supply comprises a first power source arranged on the static device part and a first energy transmission path, wherein the ancillary power supply comprises a second power source arranged on the static device part and a second energy transmission path, and wherein the first energy transmission path and the second energy transmission path are designed to transmit power from the static device part to the movable device part. In particular, in this case in the operating state the primary power supply supplies all the consumer loads on the movable device part which are essential to operation.

In view of the limited space available on the movable device part is it particularly advantageous here not to implement a power supply to the detector for maintaining a thermodynamic equilibrium in the active material by way of structural changes to the existing primary power supply in the movable device part but to arrange components having a high space requirement of such a power supply, such as for example transformers and/or converters, on the static device part.

The detector is expediently arranged to be electrically insulated from its surroundings. In particular, this means that no transmission of electricity between the detector and its surroundings is possible other than by way of the primary power supply or the ancillary power supply. This makes it possible to isolate the detector completely from the remainder of the imaging medical device if a corresponding protective circuit is incorporated.

Such a protective circuit is preferably arranged on the primary power supply on the detector, which protective circuit is designed to prevent, in other words to massively suppress, a return power flow from the detector to the remainder of the device, for example over a line for the primary power supply, such that only minimal leakage currents or residual voltages still pass from the detector to the remainder of the device.

In an advantageous embodiment of the invention, the second energy transmission path comprises an energy-delivering component arranged on the static device part and an energy-receiving component arranged on the movable device part, in which case the energy-delivering component and the energy-receiving component are situated opposite one another in an idle position.

An energy-delivering component or energy-receiving component is understood here in each case to be a component which delivers or receives energy while the ancillary power supply is operating. The idle position is given in this case precisely through the position in which the energy-delivering component and the energy-receiving component are situated opposite one another. In particular, the energy-delivering component and the energy-receiving component can in this case each comprise an electrical contact for energy transmission. This makes it possible in particular to dimension the energy-receiving component in space-saving fashion on the movable device part and arrange it as close as possible to the detector.

The energy-delivering component and the energy-receiving component of the second energy transmission path preferably each comprise an induction coil. This enables an inductive and thus contactless transmission of energy to the detector by the ancillary power supply.

In a further advantageous embodiment of the invention, the imaging medical device is designed as a computed tomography system, wherein the static device part comprises a retaining frame, wherein the movable device part comprises a rotating assembly, and wherein the computed tomography system has a control unit which is designed to transport the movable device part into an idle position when the primary power supply is switched off. A computed tomography system configured in such a manner in particular offers the advantage of being able to hold the detector permanently in operational readiness with a comparatively low power draw.

A voltage is preferably applied to the detector in the non-operating state of the imaging medical device in order to maintain a thermodynamic equilibrium in the active material of the detector. In particular, in materials such as for example cadmium telluride or cadmium zinc telluride such a state of equilibrium is characterized by a defined distribution of impurities, which can be influenced significantly by the application of a voltage.

In the non-operating state of the imaging medical device a temperature is preferably set on the detector by heating or cooling in order to maintain a thermodynamic equilibrium in the active material of the detector. A state of thermodynamic equilibrium can often be kept favorably stable by means of a specific temperature.

It further proves to be advantageous if the active material of the detector is illuminated in the non-operating state of the imaging medical device in order to maintain a thermodynamic equilibrium in the active material. The consequence of such an illumination is inter alia an increased current in the detector. By this means a thermodynamic and/or electrodynamic distribution function in the active material of the detector is deflected to such an extent that a new condition of equilibrium is established which is no longer significantly influenced in an image capture operation by incident radiation, in particular X-rays. This contributes to the serviceability of the active material.

The movable device part is advantageously transported into a defined idle position during the transition of the imaging medical device from the operating state into the non-operating state. Such a defined idle position permits the use of a particularly simple energy transmission path because components for delivering and receiving energy can be dimensioned economically corresponding to the positional accuracy, thereby reducing costs.

FIG. 1 shows a schematic diagram of an imaging medical device 1 which is designed as a computed tomography system 2. In this situation the computed tomography system 2 comprises a movable device part 5 designed as a rotating assembly 4 and a static device part 7 designed as a retaining frame 6. The detector 10 is arranged on the rotating assembly 4 in electrical insulation 12.

On the rotating assembly 4 an X-ray source 14, a fan 16, an image processing unit 18 and a control electronics unit 20 are connected in electrically conductive fashion to a central power distributor 22, from which a line 24 also leads to the detector 10. The image processing unit 18 is connected by way of an optical signal cable 19 to the detector 10. In the X-ray source 14 are furthermore provided a motor 26 for a rotating anode, a cathode heater 28 and a cooler 30. The central power distributor 22 is connected to a first energy transmission path 32, the energy-receiving component 34 whereof routes power to the central power distributor 22. The energy-delivering component 36, arranged on the retaining frame 6, of the first energy transmission path 32 is connected to a first power source 38. The first power source 38, the first energy transmission path 32 and the central power distributor 22 together with the corresponding connecting lines form the significant components of the primary power supply 40.

A layer of active material 42 which can be placed under voltage by a voltage source 44 and cooled by a cooler 46 is applied in the detector 10. The voltage source 44 and the cooler 46 are connected to a protective circuit 48 of the detector 10. A conducting connection leads therefrom to the energy-receiving component 50 of a second energy transmission path 52 arranged inside the insulation 12, and a further line leads to the central power distributor 22 of the primary power supply 40. The energy-delivering component 54 of the second energy transmission path 52 arranged on the retaining frame 6 is connected to a second power source 56. The second power source 56 and the second energy transmission path 52 together with the corresponding connecting lines form the significant components of the ancillary power supply 58. The energy-receiving component 50 and the energy-delivering component 54 of the second energy transmission path 52 each comprise an induction coil 60, 62.

During operation of the computed tomography system 2 all the significant consumer loads on the rotating assembly 4, in other words the X-ray source 14 (with the motor 26 for the rotating anode, the cathode heater 28 and the cooler 30), the detector 10 (with the voltage source 44 and the cooler 46), the fan 16, the image processing unit 18 and the control electronics unit 20 are supplied by way of the primary power supply 40. In this case the power supply for the detector 10 is routed by way of the protective circuit 48. The active material 42 of the detector 10 is kept in a thermodynamic equilibrium by a voltage from the voltage source 44 and a temperature set by the cooler 46 in order to remain serviceable.

If the computed tomography system 2 is now to be transferred into the non-operating state, for example at the end of a day of operation, an external control unit 64 which is arranged on the retaining frame 6 ensures that the rotating assembly 4 is transported into an idle position in which the induction coils 60 and 62 of the second energy transmission path 52 are situated opposite one another. After the image processing unit 18 and the control electronics unit 20 have been safely powered down, the ancillary power supply 58 can be switched on and the primary power supply 40 switched off, in which case the protective circuit 48 ensures a smooth transition of the supply in the detector 10.

In the non-operating state the active material 42 of the detector 10 continues to be held in the thermodynamic equilibrium by a voltage from the voltage source 44 and a temperature set by the cooler 46, in which case the power is now fed by way of the ancillary power supply 58.

On account of the electrical insulation 12 and the protective circuit 48 the rotating assembly, apart from the detector 10 itself, is voltage-free in the non-operating state, meaning that maintenance or repair tasks which do not concern the detector 10 can also be carried out during this time.

Although the invention has been illustrated and described in detail by means of the preferred example embodiment, the invention is not restricted by the example embodiment. Other variations can be derived therefrom by the person skilled in the art without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An imaging medical device, comprising:
   a detector including an active material, serviceable in a state of thermodynamic equilibrium;
   a primary power supply, designed to supply the imaging medical device with power in an operating state; and
   an ancillary power supply, designed to maintain a thermodynamic equilibrium in the active material of the detector in a non-operating state of the imaging medical device in order to keep the detector in a state of readiness.

2. The imaging medical device of claim 1, wherein the detector is designed as an X-ray detector.

3. The imaging medical device of claim 1, further comprising:
   at least one device for at least one of heating and cooling, including a connection to the ancillary power supply and arranged on the detector.

4. The imaging medical device of claim 1, further comprising:
   a static device part and a movably mounted device part attached thereto, wherein the detector is arranged on the movable device part, wherein the primary power supply comprises a first power source arranged on the static device part and a first energy transmission path, wherein the ancillary power supply comprises a second power source arranged on the static device part and a second energy transmission path, and wherein the first energy transmission path and the second energy transmission path are designed to transmit power from the static device part to the movable device part.

5. The imaging medical device of claim 1, wherein the detector is arranged to be electrically insulated from its surroundings.

6. The imaging medical device of claim 1, wherein the primary power supply includes a protective circuit on the detector, designed to suppress a return power flow from the detector.

7. The imaging medical device of claim 4, wherein the second energy transmission path comprises an energy-delivering component arranged on the static device part and an energy-receiving component arranged on the movable device part, and wherein the energy-delivering component and the energy-receiving component are situated opposite one another in an idle position.

8. The imaging medical device of claim 7, wherein the energy-delivering component and the energy-receiving component of the second energy transmission path each comprise an induction coil.

9. The imaging medical device of claim 4, designed as a computed tomography system, wherein the static device part comprises a retaining frame, wherein the movable device part comprises a rotating assembly, and wherein the computed tomography system includes a control unit designed to transport the movable device part into an idle position when the primary power supply is switched off.

10. A method for operating an imaging medical device including a detector including an active material, serviceable in a state of thermodynamic equilibrium; a primary power supply, designed to supply the imaging medical device with power in an operating state; and an ancillary power supply, designed to maintain a thermodynamic equilibrium in the active material of the detector in a non-operating state of the imaging medical device in order to keep the detector in a state of readiness, the method comprising:
    supplying, in the operating state, the imaging medical device with power via the primary power supply; and
    maintaining, in the non-operating state, a thermodynamic equilibrium in the active material of the detector, with power supplied by the ancillary power supply, and thereby keeping the detector in a state of readiness.

11. The method of claim 10, wherein a voltage is applied to the detector in the non-operating state of the imaging medical device to maintain a thermodynamic equilibrium in the active material of the detector.

12. The method of claim 10, wherein in the non-operating state of the imaging medical device, a temperature is set on the detector by heating or cooling, to maintain a thermodynamic equilibrium in the active material of the detector.

13. The method of claim 10, wherein the active material of the detector is illuminated in the non-operating state of the imaging medical device to maintain a thermodynamic equilibrium in the active material.

14. The method of claim 10, wherein the an imaging medical device further includes a static device part and a movably mounted device part attached thereto, wherein the detector is arranged on the movable device part, wherein the primary power supply comprises a first power source arranged on the static device part and a first energy transmission path, wherein the ancillary power supply comprises a second power source arranged on the static device part and a second energy transmission path, and wherein the first energy transmission path and the second energy transmission path are designed to transmit power from the static device part to the movable device part, the method further comprising:
    transporting the movable device part into a defined idle position during the transition of the imaging medical device from the operating state into the non-operating state.

15. The imaging medical device of claim 2, further comprising:
    at least one device for at least one of heating and cooling, including a connection to the ancillary power supply and arranged on the detector.

16. The imaging medical device of claim 2, further comprising:
    a static device part and a movably mounted device part attached thereto, wherein the detector is arranged on the movable device part, wherein the primary power supply comprises a first power source arranged on the static device part and a first energy transmission path, wherein the ancillary power supply comprises a second power source arranged on the static device part and a second energy transmission path, and wherein the first energy transmission path and the second energy transmission path are designed to transmit power from the static device part to the movable device part.

17. The imaging medical device of claim 7, designed as a computed tomography system, wherein the static device part comprises a retaining frame, wherein the movable device part comprises a rotating assembly, and wherein the computed tomography system includes a control unit designed to transport the movable device part into an idle position when the primary power supply is switched off.

18. The method of claim 11, wherein in the non-operating state of the imaging medical device, a temperature is set on the detector by heating or cooling, to maintain a thermodynamic equilibrium in the active material of the detector.

* * * * *